United States Patent
Gharpure et al.

(10) Patent No.: US 8,030,480 B2
(45) Date of Patent: Oct. 4, 2011

(54) COST-EFFECTIVE PROCESS FOR PREPARATION OF MANUFACTURE OF IRON SUCROSE

(75) Inventors: Milind Moreshwar Gharpure, Pimpri (IN); Baburao Manikrao Bhawal, Pimpri (IN); Rajiv Pandurag Sutar, Pimpri (IN); Satish Ramanlal Mehta, Pimpri (IN)

(73) Assignee: Emcure Pharmaceuticals Limited, Bhosari, Pune, Maharashtra (IN)

( * ) Notice: Subject to any disclaimer, the term of this patent is extended or adjusted under 35 U.S.C. 154(b) by 483 days.

(21) Appl. No.: 11/720,900

(22) PCT Filed: Dec. 2, 2005

(86) PCT No.: PCT/IB2005/003629
§ 371 (c)(1),
(2), (4) Date: Aug. 7, 2009

(87) PCT Pub. No.: WO2006/061685
PCT Pub. Date: Jun. 15, 2006

(65) Prior Publication Data
US 2009/0299052 A1    Dec. 3, 2009

(30) Foreign Application Priority Data
Dec. 6, 2004  (IN) .................. 1298/MUM/2004

(51) Int. Cl.
*C07H 23/00*  (2006.01)
(52) U.S. Cl. ...................................................... 536/121
(58) Field of Classification Search ................... 536/121
See application file for complete search history.

(56) References Cited

U.S. PATENT DOCUMENTS

| | | | |
|---|---|---|---|
| 3,821,192 A * | 6/1974 | Montgomery et al. | 536/103 |
| 4,746,730 A | 5/1988 | De Ambrosi et al. | 530/385 |
| 4,994,283 A | 2/1991 | Mehansho et al. | 426/74 |
| 7,169,359 B2 * | 1/2007 | Helenek et al. | 422/68.1 |
| 2003/0216566 A1 | 11/2003 | Kumari et al. | 536/123.13 |
| 2004/0038416 A1 | 2/2004 | Helenek et al. | 436/74 |
| 2005/0123504 A1 | 6/2005 | Helenek et al. | 424/78.17 |
| 2005/0209187 A1 | 9/2005 | Newton et al. | 514/53 |

FOREIGN PATENT DOCUMENTS

| | | |
|---|---|---|
| CA | 1 253 821 A | 5/1989 |
| IN | 187116 | 2/2002 |
| WO | WO 2005/000210 A2 | 1/2005 |
| WO | WO 2005/094202 A2 | 10/2005 |

* cited by examiner

*Primary Examiner* — Shaojia Anna Jiang
*Assistant Examiner* — Ganapathy Krishnan
(74) *Attorney, Agent, or Firm* — Seed IP Law Group PLLC

(57) ABSTRACT

The present invention relates to a cost-effective process for manufacture of iron sucrose complex.

18 Claims, No Drawings

COST-EFFECTIVE PROCESS FOR PREPARATION OF MANUFACTURE OF IRON SUCROSE

CROSS-REFERENCE TO RELATED APPLICATIONS

This application is a national stage application filed under 35 U.S.C. 371 of International Application No. PCT/IB2005/003629, accorded an International Filing Date of Dec. 2, 2005, which claims priority to India Patent Application No. 1298/MUM/2004 filed Dec. 6, 2004. These applications are incorporated herein by reference in their entireties.

FIELD OF THE INVENTION

The present invention relates to a cost-effective process for manufacture of iron sucrose complex.

BACKGROUND OF THE INVENTION

Iron Sucrose, which belongs to the therapeutic class of haemitinic is a complex of polynuclear iron (III) hydroxide in sucrose having molecular weight approximately between 34,000 and 60,000 daltons, and structural formula $[Na_2Fe_5O_8(OH).3(H_2O)]_n.m(C_{12}H_{22}O_{11})$, where n is the degree of polymerization and m is the number of sucrose molecules associated with the iron(III) hydroxide.

Iron sucrose containing 30% sucrose (w/v) is an injectable, which is administered intravenously for replenishing body iron stores in patients with iron deficiency on chronic hemodialysis and receiving erythropoietin.

There are numerous references in prior art, which disclose methods for preparation of complexes of carbohydrates with various metals.

U.S. Pat. No. 4,746,730 (assigned to Medinianum Farmaceutci) discloses a method for preparation of complexes of iron and various carbohydrates like fructose and saccharose. The method comprises addition of an aqueous solution of ferric chloride to a fructose solution followed by addition of aqueous potassium hydroxide solution to get pH between 7.8 and 8.5. The complex is obtained by a process of lyophilisation which is very expensive on an industrial scale.

U.S. Pat. No. 4,994,283 (assigned to Procter and Gamble) discloses a method for preparing iron-sugar carbohydrate complex, which comprises initial preparation of a complex of calcium and a sugar followed by preparation of the iron-sugar complex by reaction with an iron source such as ferrous ammonium sulfate and treating the resultant iron-sugar complex with malic acid to give the desired iron-sugar complex.

The method is quite lengthy as it does not involve the direct preparation of the iron-sugar complex and rather involves the intermediary of a calcium-sugar complex from which the product is obtained. Further, there is no surety that the iron-sugar complex obtained will be free from the calcium-sugar complex.

CA 1 253 821 (assigned to Pfeifer & Langer) discloses a method for preparation of water soluble iron dextran complex comprising formation of dextran utilizing enzyme and bacteria and subsequently reacting the same with freshly prepared iron (III) hydroxide. The preparation of iron dextran utilizing enzyme and bacteria is very selective and not convenient for commercial production.

US 2003/0216566A1 (assigned to Patel, et. al) discloses a method for preparation of a complex of sodium ferric gluconate in sucrose comprising reaction of sodium gluconate with ferric oxyhydroxide to give sodium ferric gluconate which is freeze-dried. The complex thus obtained is added to sucrose solution to give sodium ferric gluconate in sucrose. Also, the choice of the base selection is critical in the process.

IN 187116 (assigned to Alkem Laboratories) teaches a method for preparing saccharated iron oxide by reaction of a ferric salt with an aqueous solution of an inorganic base to give ferric oxyhydroxide which on further treatment with sucrose at pH 6.5 to 7.5 gives saccharin iron oxide.

Although, it is mentioned in IN 187116 that saccharin iron oxide is obtained at pH 6.5 to 7.5 but it is our finding that preparation of saccharin iron oxide at pH 6.5 to 7.5 fails as there is no formation of saccharin iron oxide at the said pH.

WO 2005/094202 A2 (assigned to Navinta LLC) discloses another method for the preparation of Iron sucrose comprising of addition of an inorganic base in a phased manner to an aqueous solution of ferric salts to obtain ferric hydroxide followed by addition to an aqueous solution of sucrose and heating at a temperature of 100-105° C., followed by freeze drying of the resulting product. The iron sucrose thus obtained has to be purified to obtain the product conforming to desired specifications.

The method disclosed in this patent application utilizes freeze drying for isolating iron sucrose, which is however not suitable for industrial purpose, since the isolation method is very expensive.

WO 2005/000210 A2 discloses a general method for the preparation of iron-saccharidic complexes, including iron sucrose. The preparation of iron sucrose disclosed in this patent application involves mixing of the aqueous solution of the ferric salt and sucrose followed by addition of sodium hydroxide solution to give ferric hydroxide sucrose complex. This method has the disadvantage of the inability to monitor whether the ferric salt initially added has been completely converted to ferric hydroxide for further reaction with sucrose solution. Therefore, there is every possibility of the iron sucrose thus formed being contaminated with the ferric salts employed initially and secondly, due to the possible incomplete formation of ferric hydroxide, the yield of iron sucrose will be lower, rendering the process unsuitable for industrial applications. Further, iron sucrose thus obtained has a molecular weight around 1,570,000 daltons (Example 2), which does not conform to the specification for molecular weight desired by the regulatory authorities (34,000 to 60,000 daltons) for Iron sucrose.

Thus the prior art methods have several shortcomings such as
  i) utilization of freeze drying, which is expensive on industrial scale,
  ii) in one of the prior art methods iron sugar complex is prepared through the intermediary of the calcium complex of the carbohydrate, which is lengthy and more expensive.
  iii) glucose is required in conjunction with sucrose for preparation of the iron sucrose complex. Utilization of another carbohydrate like glucose makes the process more costly.
  iv) selection of an inorganic base for preparation of ferric oxyhydroxide is critical as inorganic bases like ammonium hydroxide or sodium hydroxide utilized for preparation of ferric oxyhydroxide fails to give the sodium ferric gluconate complex with sodium gluconate.

There is ample information about the iron complexes in the literature, however for the preparation of iron sucrose the information available is scanty.

Therefore, in view of these shortcomings there is a need for an improved method, which is not only economical and cost-effective but is also simple and overcomes the drawbacks of prior art methods to give iron sucrose complex conforming to regulatory standards.

The present inventors have a simple cost-effective method for preparation of iron-sucrose complex, which comprises reaction of a ferric salt solution with an aqueous solution of an inorganic base at pH between 3.5 and 7.0 to give ferric oxyhydroxide, which is then treated with sucrose solution at a temperature of 20-100° C. and pH 8.0 to 13.0 to give iron-sucrose complex conforming to regulatory specifications.

OBJECT OF THE INVENTION

An object of the present invention is to provide an improved method for preparation of iron sucrose complex, conforming to regulatory specifications.

Another object of the invention is to provide an improved method for preparation of iron sucrose complex, which is simple and cost-effective.

SUMMARY OF THE INVENTION

One aspect of the invention relates to an improved method for preparation of iron source complex in sucrose by a simple cost-effective method.

Another aspect of the invention relates to an improved process for preparation of iron sucrose complex in sucrose, which comprises reaction of ferric salts with an inorganic base at pH 3.5 to 7.0 to give ferric oxyhydroxide, which is then added to a solution of sucrose followed by adjusting the pH of the mixture between 9.0 and 13.0 with an inorganic base to give iron sucrose complex, which is then isolated by partial concentration of the aqueous mixture and precipitation, by addition of an organic solvent or mixture thereof to give iron sucrose complex in sucrose conforming to pharmacopoeial specification.

DETAILED DESCRIPTION OF THE INVENTION

The present invention describes the preparation of iron (III) sucrose complex in sucrose. Although, we do not wish to be bound by theory, the following is proposed as the Scheme (i.e. Scheme—1) of formation of iron (III) sucrose comprising the steps of:

Scheme-I: Method as embodied in the present invention for preparation of Iron Sucrose complex.

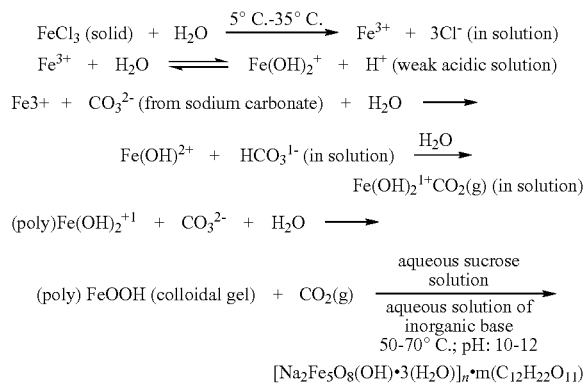

i) Preparation of ferric oxy hydroxide at a pH between 3.5 and 7.0 by addition of an inorganic base to a suspension of ferric salt in water at a temperature between 5.0° C. and 35° C.

The ferric salts are selected from a group comprising of ferric chloride, ferric bromide, ferric iodide, ferric acetate, ferric citrate, ferric nitrate, and ferric sulphate.

The preferred ferric (III) salt was ferric (III) chloride and ferric (III) nitrate either in anhydrous or hydrated form.

Ferric (III) nitrate or ferric (III) chloride was suspended in water and dissolved by stirring at room temperature.

An inorganic base or an organic base was added to the mixture. The preferred base was an inorganic base.

The inorganic base was selected from a group comprising of carbonates or hydroxides of alkali metals like sodium, potassium or alkaline earth metals like calcium, barium etc or ammonia.

The preferred inorganic base was sodium carbonate, while the preferred pH selected was between 4.0 and 6.0.

The preferred pH range was between 4.1 and 5.2.

An aqueous solution of sodium carbonate was added to the mixture.

The mixture was stirred for 60-90 minutes for complete precipitation of ferric oxyhydroxide, which was then filtered and washed with water.

The wet cake was utilized for preparing iron sucrose.

ii) Addition of ferric oxyhydroxide to an aqueous solution of sucrose at 15-40° C. and adjusting the pH of the resultant mixture with an aqueous solution of an inorganic base between 10 and 12.0, preferably between 11.3 and 12.0, followed by heating the reaction mixture between 85 to 100° C., preferably between 90-95° C. and adjusting the pH to 9.75 to 10.0, using an inorganic acid, preferably HCl. Charcoal was optionally added to the mixture, stirred and filtered. The pH of the filtrate was again adjusted between 12.0 and 12.5, preferably between 12.1±0.2 using an inorganic base.

The inorganic base utilized for adjusting pH of the reaction mixture was selected from hydroxides of alkali metals like sodium, potassium etc or alkaline earth metals like calcium, barium etc.

The preferred inorganic base was either sodium hydroxide or potassium hydroxide.

It is pertinent to mention that without the gradual adjustment of pH at selected temperature, it was not possible to obtain iron sucrose complex in sucrose conforming to pharmacopoeial specification.

iii) Isolation of iron sucrose complex by partial concentration of the aqueous solution at reduced pressure between 40° C. and 60° C., followed by addition of a single or mixture of organic solvents to the partially concentrated mixture or vice-versa to precipitate the iron sucrose complex, which is filtered and optionally washed with an organic solvent.

The reaction mixture is cooled to ambient temperature and concentrated.

The residue containing iron sucrose was added to an organic solvent.

The organic solvents employed for precipitation of the iron sucrose complex was selected from the group comprising of alcohols, ketones, ethers, amides, and sulfoxides.

The alcohol was selected from the group comprising of methanol, ethanol, isopropanol, n-propanol, isobutanol, n-butanol. The preferred alcohol was methanol.

The ketones are selected from the group comprising of acetone, methyl ethyl ketone, methyl isobutyl ketone. The preferred ketonic solvent was acetone.

The ethers are selected from the group comprising of tetrahydrofuran, dioxane and diethyl ether. The preferred ether was tetrahydrofuran.

The amides are selected from the group comprising of dimethyl formamide, dimethyl acetamide, N-methyl pyrrolidone. The preferred amide was dimethyl formamide.

The sulfoxide was dimethyl sulfoxide.

These solvents are either employed alone or in combination thereof.

Iron sucrose thus obtained was further processed by adding iron sucrose complex to aqueous water-miscible organic solvent.

The organic solvents employed for reprocessing of the iron sucrose complex was selected from the group comprising of alcohols, ketones, ethers, amides, and sulfoxides.

The alcohol was selected from the group comprising of methanol, ethanol, isopropanol, n-propanol, isobutanol, n-butanol. The preferred alcohol was methanol.

The amount of water in methanol was selected between 3.0% and 10%.

The mixture was stirred for time between 30 minutes and 300 minutes.

The mixture was filtered and dried.

The iron sucrose obtained by the above method has the desired molecular weight between 34,000 and 60,000 daltons and conforms to regulatory specifications.

The inventors during their investigations and studies found that the preparation of iron sucrose is pH sensitive and heat sensitive. Hence, the inventors have vastly improved the process that the iron sucrose thus prepared is pure and the conditions employed are such that the iron sucrose complex remains unaffected throughout and pH conditions/heat does not affect it during production stage. Further and surprisingly, the inventors found that even though pH is adjusted several times during the process, it does not affect the final product. In fact, changes in the pH at selected temperature assists in preparation of an improved product. The iron sucrose prepared as per the process of the present invention may be employed and used as an injectable or formulated in any pharmaceutically acceptable form including syrup or suspension. It may also be formulated or used as supplemented in vitamin tablets; it may also be used as food supplement.

This invention is illustrated by the following examples, but should not be construed to be limited thereto.

EXAMPLE

1. Preparation of Iron Sucrose from Ferric Chloride

Iron (III) Chloride anhydrous (100 gms, 0.6161 moles) was dissolved in distilled water (3000 ml). Added charcoal (10.0 gms) to the mixture. The reaction mass was stirred for 30 minutes, and filtered. A solution of 30% (w/v) $Na_2CO_3$ was gradually to the ferric chloride solution and the pH of the reaction mixture adjusted between 4.4 and 4.6 at 24-26° C. Filtered the slurry and washed with water. Slurry of wet cake was made in water (500 ml).

Prepared a mixture of water (500 ml) & Sucrose (900 gms; 2.629 moles). The slurry of ferric oxyhydroxide was added at 25-30° C. NaOH solution (30% w/v) was then added and pH adjusted between 11.5-11.8. The mixture was maintained for 10 min. at 25-30° C. The reaction mixture was heated to 90-95° C. and the pH adjusted to 9.85-9.95 with HCl (35%) The mixture was stirred for 2.0-3.0 hours. Added activated charcoal and stirred the mixture for about 30 minutes and filtered through 0.2 micron filter. Readjusted the pH to 12.2-12.3 with 30% NaOH solution at 25-30° C. and concentrated under reduced pressure. In another flask charged methanol (5000 ml) and added concentrated mass to obtain iron sucrose and filtered it, washed with methanol (1000 ml) and acetone (1000.0 ml).

Yield: 420 gms.

2. Purification of Iron Sucrose

Iron sucrose complex (1700 gms) was added to a mixture of methanol (6975 ml) and water (525 ml) at 25-30° C. and stirred for 120 minutes. The mixture was filtered, washed with acetone (1500 ml) and dried.

Yield: 1300 gms.

We claim:

1. A process of preparing an iron sucrose complex having a molecular weight between 34,000 and 60,000 daltons, comprising the steps of:
   (a) reacting a ferric salt with a base in a solvent at a pH between 4.0 and 6.0 to form ferric oxyhydroxide and isolating the ferric oxyhydroxide as a slurry;
   (b) adding the ferric oxyhydroxide slurry to an aqueous solution of sucrose and adjusting the pH of the reaction mixture to between 11.3 and 12.0 with an aqueous solution of an inorganic base at a temperature between 15° C. and 40° C. to form a reaction mixture;
   (c) heating the reaction mixture to a temperature between 85° C. and 100° C., adjusting the pH of the reaction mixture to between 9.75 and 10.0 and stirring the reaction mixture for a period of time from 2 to 3 hours to form the iron sucrose complex; and
   (d) isolating the iron sucrose complex from the reaction mixture by adjusting the pH of the reaction mixture between 12.0 and 12.5, concentrating the reaction mixture, adding the concentrated reaction mixture to an organic solvent or adding an organic solvent to the concentrated reaction mixture, and filtering.

2. The process according to claim 1, where in step (b), the pH is adjusted to between 11.5 and 11.8.

3. The process according to claim 1, where in step (c), the pH is adjusted between 9.85 and 9.95.

4. The process according to claim 1, where in step (d), the pH is adjusted between 12.20 and 12.30.

5. The process according to claim 1, where in step (b), the temperature is between 20° C. and 35° C.

6. The process according to claim 5, where the temperature is between 25° C. and 30° C.

7. The process according to claim 1, wherein in step (c), the temperature is between 90° C. and 100° C.

8. The process according to claim 7, wherein the temperature is between 90° C. and 95° C.

9. The process according to claim 1, where in step (d), the temperature is between 15° C. and 40° C.

10. The process according to claim 9, where the temperature is between 25° C. and 30° C.

11. The process according to claim 1, further comprising the steps of:
   a) adding the isolated iron sucrose complex to an aqueous water-miscible organic solvent to form a mixture,
   b) stirring the mixture at ambient temperature for a time duration between 30 minutes and 300 minutes,
   c) filtering and drying the mixture.

12. The process according to claim 1 or claim 11, wherein the organic solvent is an alcohol.

13. The process according to claim 12, wherein the alcohol is selected from the group consisting of methanol, ethanol, isopropanol, n-propanol, isobutanol and n-butanol.

14. The process according to claim 13, wherein the alcohol is methanol.

15. The process according to claim 11, wherein the amount of water in the aqueous water-miscible organic solvent is between 3% and 10%.

16. A process of preparing iron sucrose complex in sucrose where the iron sucrose complex has a molecular weight of between 34,000 and 60,000 daltons, comprising the steps of:
 a) reacting sucrose and ferric oxyhydroxide in an aqueous medium comprising of sodium ions, initially at a pH between 11.3 and 12.0 at an initial temperature between 15° C. and 40° C., followed by heating to a temperature between 85° C. and 100° C. and adjusting pH between 9.75 and 10.00, and
 b) isolating iron sucrose complex in sucrose from the reaction mixture by adjusting pH between 12.0 and 12.5, concentrating and adding to it an organic solvent or reversely adding the organic solvent to the concentrated reaction mixture and filtering.

17. The process according to claim 16, where in step (a) the initial temperature is between 20° C. and 35° C.

18. The process according to claim 16, where in step (a) the temperature is between 90° C. and 95° C.

* * * * *